United States Patent [19]

Lauffer et al.

[11] Patent Number: 4,937,239

[45] Date of Patent: Jun. 26, 1990

[54] AZABICYCLOALKANE OXIME & AZABICYCLOALKENE OXIME MUSCARINIC AGENTS

[75] Inventors: David J. Lauffer, Saline; Walter H. Moos; Hasile Tecle, both of Ann Arbor, all of Mich.

[73] Assignee: Warner-Lambert Company, Morris Plains, N.J.

[21] Appl. No.: 310,229

[22] Filed: Feb. 13, 1989

[51] Int. Cl.$^5$ .................... A61K 31/55; C07D 453/02; C07D 487/08

[52] U.S. Cl. ................................. 514/183; 514/214; 514/305; 514/413; 540/477; 540/582; 546/133; 546/137; 548/453

[58] Field of Search ................ 546/133, 137; 540/582, 540/477; 548/453; 514/413, 305, 214, 183

[56] References Cited

FOREIGN PATENT DOCUMENTS 0316718 5/1989 European Pat. Off. .
0338723 10/1989 European Pat. Off. .

OTHER PUBLICATIONS

*Chemical Abstracts,* 64:12642e(1966)[L. Mastafanova, et al., *Khim. Geterotsikl. Soedin., Akad. Navk Latv. SSR* 1965(6), 858–863].
*Chemical Abstracts,* 68:48774m (1968)[H. Fischer, et al., *Helv. Chim. ACTA 51(1),* 153–163 (1968)].
*Chemical Abstracts,* 90:38202p (1979)[K. Becker, et al., *Helv. Chim. ACTA* 1978, 61(7), 2596–2606].
*Chemical Abstracts,* 110:134964r (1989)[Evr. Pat. Appl. EP 264,091, T. Kamiya et al., 4/20/88.]
March, J. Advanced Organic Chemistry, McGraw Hill, New York, 1968, p. 675.

*Primary Examiner*—Richard A. Schwartz
*Attorney, Agent, or Firm*—Ruth N. Newtson

[57] ABSTRACT

Novel 1-azabicycloalkane- and alkene-oximes (Ia) and 8-azabicyclo[3.2.1]octane- and octene-oximes (Ib) are provided, these compounds being useful as agents for treating pain or for treating the symptoms of senile cognitive decline. Also provided are pharmaceutical compositions containing the compounds and methods of treatment using the compounds in dosage form.

11 Claims, No Drawings

AZABICYCLOALKANE OXIME & AZABICYCLOALKENE OXIME MUSCARINIC AGENTS

BACKGROUND OF THE INVENTION

The present invention relates to chemical compounds, pharmaceutical compositions, and to a method of treatment employing the compounds and compositions. More particularly, the invention concerns certain oxide compounds, namely 1-azabicycloalkane oximes and azabicycloalkene oximes, pharmaceutical compositions containing these compounds, and a pharmaceutical method of treatment.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia, for example, the level of the enzyme choline acetyltransferase (CAT) can be reduced by as much as ninety percent. (See Davies, et al, The Lancet, 1976 (Vol. 2): 1403; Perry, et al, J. Neurol. Sci., 34: 247–265 (1977); and White et al, The Lancet, 1977 (Vol. 1): 668–670).

Since CAT catalyzes the synthesis of acetylcholine from its precursors choline and acetyl Coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory.

The cholinergic hypothesis of aging and dementia suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, Neurobiol. Aging, 4: 25–30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the releases of acetylcholine from presynaptic nerve terminals, thus increasing synaptic acetylcholine. (See H. P. Davis, et al, Exp. Aging Res., 9: 211–214 (1983)).

It has been known for some time that the natural alkaloid, muscarine, has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Arecoline (the methyl ester of 1,2,5,6-tetrahydro-1-methyl-3-pyridinecarboxylic acid) is the chief alkaloid found in betel nuts (Areca catechu). Betel nuts have been chewed by natives of the East Indies since early times as a euphoretic. The present pharmaceutical utility of arecoline, however, has been limited to its use as a veterinary anthelmintic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double blind study. (See Christie, et al, Brit. J. Phychiatry, 138: 46–50 (1981)).

Regarding analgesia, the literature indicates that acetylcholine and muscarine agonists possess antinociceptive activity (see T. T. Chau, et al, J. Pharmacol. Exp. Ther., 222: 612–666 (1982); W. L. Dewey, et al, Life Sci., 17: 9–10 (1975); and N. W. Pedigo, et al, Neurosci. Lett., 26: 85–90 (1981) and references cited therein).

SUMMARY OF THE INVENTION

The present invention provides, in its broadest chemical compound aspect, azabicyclo ring compounds of Formula Ia and Formula Ib:

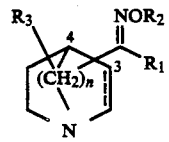

Ia

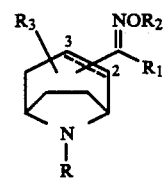

Ib wherein the —C(=NOR₂)R₁ group is attached at either carbon atom number three or four (Ia) or two or three (Ib) of the azabicyclo ring, and the attachment of the OR₂ group to the nitrogen atom is configured either Z (i.e., cis) or E (i.e., trans) to the azabicyclo ring; Ia and Ib each may be mixtures of E and Z isomers; n is an integer from 1 to 4;

R is hydrogen or alkyl of from one to six carbon atoms;

$R_1$ is hydrogen; alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to eight carbon atoms; —A—C(=O)—O—R_4 where A is a bond or is a hydrocarbon chain of from one to four carbon atoms and when containing two or more carbon atoms may contain one double bond and where $R_4$ is alkyl of from one to six carbon atoms; or

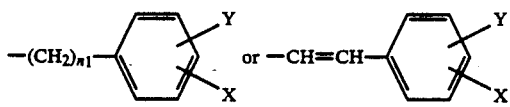

where $n_1$ is zero to four and X' and Y' are independently selected from hydrogen, fluorine, chlorine, bromine, hydroxy, straight or branched alkyl of from one to three carbon atoms, or alkoxyl of from one to four carbon atoms;

$R_2$ is hydrogen; alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to six carbon atoms; or

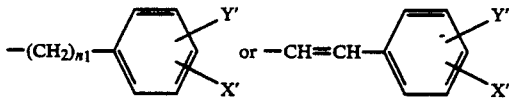

where $n_1$ is zero to four and X' and Y' are independently selected from hydrogen, fluorine, chlorine, bromine, hydroxy, alkyl of from one to three carbon atoms, and alkoxyl of from one to four carbon atoms; alkylcarbonyl of from two to twelve carbon atoms; alkenylcarbonyl of from three to twelve carbon atoms; alkynylcarbonyl of from three to twelve carbon atoms; or —C(=O)—NR_5 R_6 where $R_5$ and $R_6$ are independently selected from hydrogen, alkyl of from one to four carbon atoms or phenyl;

$R_3$ is hydrogen; alkyl of from one to six carbon atoms; hydroxy; alkoxyl of from one to four carbon atoms; alkylcarbonyl of from two to twelve carbon atoms; $NH_2$; $NH(C_{1-4}alkyl)$, e.g. methylamino; $N(C_{1-4}alkyl)_2$, e.g. dimethylamino or methylethylamino; $NHCO(C_{1-4}alkyl)$, e.g. acetamido; or $NHCOOCH_3$;

or a pharmaceutically acceptable acid addition salt thereof.

In another aspect, the present invention provides pharmaceutical compositions useful as analgesic agents comprising an analgesically effective amount of a compound as defined above in combination with a pharmaceutically acceptable carrier.

In another aspect, the present invention provides pharmaceutical compositions for treating the symptoms of senile cognitive decline comprising a cholinergically effective amount of a compound as defined above in combination with a pharmaceutically acceptable carrier.

In another aspect, the present invention provides a method of alleviating pain in a mammal comprising administering to a mammal in need of such treatment an analgesically effective amount of a compound as defined above in combination with a pharmaceutically acceptable carrier.

In yet another aspect, the present invention provides a method of treating the symptoms of senile cognitive decline in the elderly characterized by decreased cerebral acetylcholine production or release comprising administering to a patient in need of such treatment a cholinergically effective amount of a compound as defined above in combination with a pharmaceutically acceptable carrier.

DETAILED DESCRIPTION

The compounds of the present invention comprise a class of azabicycloalkane oximes and azabicycloalkene oximes and their pharmaceutically acceptable salts which are centrally acting muscarinic agents and which are thus useful as analgesic agents, sleep aids, or therapeutic agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

The term "alkyl of from one to six carbon atoms" denotes a substituent group derived from a saturated hydrocarbon by removal of a single hydrogen atom. The term includes methyl, ethyl, n-propyl, iso-propyl, n-butyl, sec-butyl, iso-butyl, tert-butyl, and the various isomeric forms of pentyl and hexyl. Likewise, the terms "alkenyl of from one to six carbon atoms" and "alkynyl of from one to six carbon atoms" denote substituent groups derived, respectively, from alkene or alkyne hydrocarbons by the removal of a single hydrogen atom. These terms include ethenyl, ethynyl, propenyl, propynyl, and similar branched and unsaturated hydrocarbon groups of up to six carbon atoms.

The term "cycloalkyl of from three to eight carbon atoms" denotes saturated carbocyclic rings such as cyclopropyl, cyclobutyl, cyclopentyl, cyclohexyl, as well as alkyl substituted carbocyclic rings containing up to eight carbon atoms such as methyl-, dimethyl-, and ethylcyclohexyl.

The terms "alkoxy" or "alkoxyl" denote a substituent group derived by removal of the hydrogen from the oxygen atom of a saturated alcohol and attached to the parent molecular moiety through the oxygen atom. Such groups include methoxyl, ethoxyl, 1- and 2-propoxyl, and similar branched and unbranched alkoxyl groups of up to four carbon atoms.

The terms "alkylcarbonyl," "alkenylcarbonyl," and "alkynylcarbonyl" denote substituent alkyl, alkenyl, or alkynyl groups as previously defined, attached to the parent molecular moiety through a carbonyl group.

The compounds of the present invention may exist in either of two isomeric forms in which the oxygen atom of the oxime group and its attached substituent, $R_2$ may be either syn- or anti- with respect to the azabicyclo ring systems. The present invention includes both forms of the compounds as well as mixtures of the syn- and anti- forms. In those compounds in which there is a double bond in a carbon chain, both the Z (i.e. cis) and E (i.e. trans) forms are included in the present invention. The terms syn- and anti- as they apply to the compounds of the present invention are illustrated by Formulas IIa and IIb:

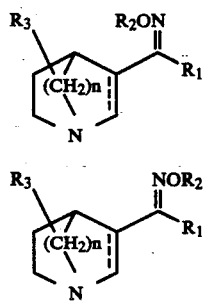

Examples of compounds contemplated as falling within the scope of the present invention include, but are not limited to the following:
1-Azabicyclo[2.2.2]octane-3-carboxaldehyde, oxime
1-Azabicyclo[2.2.2]octane-3-carboxaldehyde, O-methyloxime
1-Azabicyclo[2.2.2]oxtane-3-carboxaldehyde, O-ethyloxime
1-Azabicyclo[2.2.2]octane-3-carboxaldehyde, O-2-propenyloxime
1-Azabicyclo[2.2.2]octane-3-carboxaldehyde, O-2-propynyloxime
1-Azabicyclo[2.2.2]oct-2-ene-3-carboxaldehyde, oxime
1-Azabicyclo[2.2.2]oct-2-ene-3-carboxaldehyde, O-methyloxime
1-Azabicyclo[2.2.2]oct-2-ene-3-carboxaldehyde, O-ethyloxime
1-Azabicyclo[2.2.2]oct-2-ene-3-carboxaldehyde, O-2-propenyloxime
1-Azabicyclo[2.2.2]oct-2-ene-3-carboxaldehyde, O-2-propynyloxime
Ethanone,1-(1-Azabicyclo[2.2.2]oct-3-yl)-, oxime
Ethanone,1-(1-Azabicyclo[2.2.2]oct-3-yl)-, O-methyloxime
Ethanone,1-(1-Azabicyclo[2.2.2]oct-3-yl)-, O-ethyloxime
Ethanone,1-(1-Azabicyclo[2.2.2]oct-3-yl)-, O-2-propenyloxime
Ethanone,1-(1-Azabicyclo[2.2.2]oct-3-yl)-, O-2-propynyloxime
Ethanone,1-(1-Azabicyclo[2.2.2]oct-2-ene-3-yl)-, oxime
Ethanone,1-(1-Azabicyclo[2.2.2]oct-2-ene-3-yl)-, O-methyloxime
Ethanone,1-(1-Azabicyclo[2.2.2]oct-2-ene-3-yl)-, O-ethyloxime
Ethanone,1-(I-Azabicyclo[2.2.2]oct-2-ene-3-yl)-, O-2-propenyloxime
Ethanone,1-(1-Azabicyclo[2.2.2]oct-2-ene-3-yl)-, O-2-propynyloxime
Ethanone,1-(3-hydroxy-1-Azabicyclo[2.2.2]oct-3-yl)-, oxime
Ethanone,1-(3-hydroxy-1-Azabicyclo[2.2.2]oct-3-yl)-, O-methyloxime
Ethanone,1-(3-hydroxy-1-Azabicyclo[2.2.2]oct-3-yl)-, O-ethyloxime
Ethanone,1-(3-hydroxy-1-Azabicyclo[2.2.2]oct-3-yl)-, O-2-propenyloxime
Ethanone,1-(3-hydroxy-1-Azabicyclo[2.2.2]oct-3-yl)-, O-2-propynyloxime
Ethanone,1-(3-methoxy-1-Azabicyclo[2.2.2]oct-3-yl)-, oxime
Ethanone,1-(3-methoxy-1-Azabicyclo[2.2.2]oct-3-yl)-, O-methyloxime
Ethanone,1-(3-methoxy-1-Azabicyclo[2.2.2)oct-3-yl)-, O-ethyloxime
Ethanone,1-(3-methoxy-1-Azabicyclo[2.2.2]oct-3-yl)-, O-2-propynyloxime
Ethanone,1-(3-methoxy-1-Azabicyclo[2.2.2]oct-3-yl)-, O-2-propynyloxime
Ethanone,1-(3-acetoxy-1-Azabicyclo[2.2.2]oct-3-yl)-, oxime
Ethanone,1-(3-acetoxy-1-Azabicyclo[2.2.2]oct-3-yl)-, O-methyloxime
Ethanone,1-(3-acetoxy-1-Azabicyclo[2.2.2]oct-3-yl)-, O-ethyloxime
Ethanone,1-(3-acetoxy-1-Azabicyclo[2.2.2]oct-3-yl)-, O-2-propenyloxime
Ethanone,1-(3-acetoxy-1-Azabicyclo[2.2.2]oct-3-yl)-, O-2-propynyloxime
1-Azabicyclo[2.2.1]heptane-3-carboxaldehyde, oxime
1-Azabicyclo[2.2.1]heptane-3-carboxaldehyde, O-methyloxime
1-Azabicyclo[2.2.1]heptane-3-carboxaldehyde, O-ethyloxime
1-Azabicyclo[2.2.1]heptane-3-carboxaldehyde, O-2-propenyloxime
1-Azabicyclo[2.2.1]heptane-3-carboxaldehyde, O-2-propynyloxime
1-Azabicyclo[2.2.1]hept-2-ene-3-carboxaldehyde, oxime
1-Azabicyclo[2.2.1]hept-2-ene-3-carboxaldehyde, O-methyloxime
1-Azabicyclo[2.2.1]hept-2-ene-3-carboxaldehyde, O-ethyloxime
1-Azabicyclo[2.2.1]hept-2-ene-3-carboxaldehyde, O-2-propenyloxime
1-Azabicyclo[2.2.1]hept-2-ene-3-carboxaldehyde, O-2-propynyloxime
Ethanone,1-(1-Azabicyclo[2.2.1]hept-3-yl)-, oxime
Ethanone,1-(1-Azabicyclo[2.2.1]hept-3-yl)-, O-methyloxime
Ethanone,1-(1-Azabicyclo[2.2.1]hept-3-yl)-, O-ethyloxime
Ethanone,1-(1-Azabicyclo[2.2.1]hept-3-yl)-, O-2-propenyloxime
Ethanone,1-(1-Azabicyclo[2.2.1]hept-3-yl)-, O-2-propynyloxime
Ethanone,1-(1-Azabicyclo[2.2.1]hept-2-ene-3-yl)-, oxime
Ethanone,1-(1-Azabicyclo[2.2.1]hept-2-ene-3-yl)-, O-methyloxime
Ethanone,1-(1-Azabicyclo[2.2.1]hept-2-ene-3-yl)-, O-ethyloxime
Ethanone,1-(1-Azabicyclo[2.2.1]hept-2-ene-3-yl)-, O-2-propenyloxime
Ethanone,1-(1-Azabicyclo[2.2.1]hept-2-ene-3-yl)-, O-2-propynloxime
8-Methyl-8-azabicyclo[3.2.1]octane-2-carboxaldehyde, oxime
8-Methyl-8-azabicyclo[3.2.1]octane-2-carboxaldehyde, O-methyloxime
8-Methyl-8-azabicyclo[3.2.1]octane-2-carboxaldehyde, O-ethyloxime
8-Methyl-8-azabicyclo[3.2.1]octane-2-carboxaldehyde, O-2-propenyloxime
8-Methyl-8-azabicyclo[3.2.1]octane-2-carboxaldehyde, O-2-propynyloxime 8-Methyl-8-azabicyclo[3.2.1]oct-2-ene-2-carboxaldehyde-, oxime 8-Methyl-8-azabicyclo[3.2.1]oct-2-ene-2-carboxaldehyde, O-methyloxime 8-Methyl-8-azabicyclo[3.2.1]oct-2-ene-2-carboxaldehyde, O-ethyloxime 8-Methyl-8-azabicyclo[3.2.1]oct-2-ene-2-carboxaldehyde, O-2-propenyloxime 8-Methyl-8-azabicyclo[3.2.1]oct-2-ene-2-carboxaldehyde, O-2-propynyloxime Ethanone,1-(8-methyl-8-azabicyclo[3.2.1]oct-2-yl)-, oxime Ethanone,1-(8-methyl-8-azabicyclo[3.2.1]oct-2-yl)-, O-methyloxime Ethanone,1-(8-methyl-8-azabicyclo[3.2.1]oct-2-yl-, O-ethyloxime Ethanone,1-(8-methyl-8-azabicyclo[3.2.1]oct-2-yl)-, O-2-propenyloxime Ethanone,1-(8-methyl-8-azabicyclo[3.2.1]oct-2-yl)-, O-2-propynyloxime Ethanone,1-(8-methyl-8-azabicyclo[3.2.1]oct-2-ene-3-yl), oxime Ethanone,1-(8-methyl-8-azabicyclo[3.2.1]oct-2-ene-3-yl)-, O-methyloxime Ethanone,1-(8-methyl-8-azabicyclo[3.2.1]oct-2-ene-3-yl)-, O-ethyloxime Ethanone,1-(8-methyl-8-azabicyclo[3.2.1]oct-2-ene-3-yl)-, O-2-propenyloxime Ethanone,1-(8-methyl-8-azabicyclo[3.2.1]oct-2-ene-3-yl)-, O-2-propynyloxime Compounds of the present invention are prepared by the general synthetic method detailed in Reaction Sequence 1, following.

Referring to Reaction Sequence 1, the requisite starting azabicyclocarboxylic acid esters 1 and 4 are converted to the corresponding aldehydes ($R_1$=H) and ketones ($R_1$=alkyl) 2 and 5. These are reacted with the appropriate hydroxylamines to give the corresponding azabicycloald- and ketoximes.

REACTION SEQUENCE 1

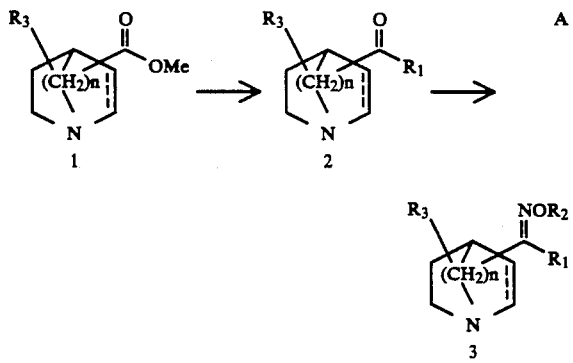

REACTION SEQUENCE 1 —continued

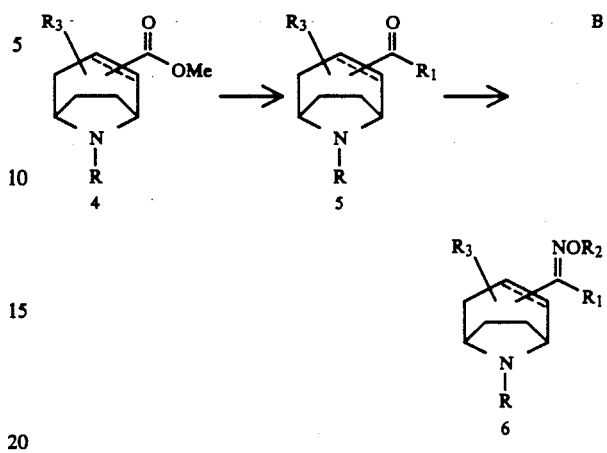

By virtue of the basic nitrogen atom in the azabicyclo ring, the compounds of the present invention form pharmaceutically acceptable acid addition salts with organic and inorganic acids. Examples of suitable acids for the formation of pharmaceutically acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane- and ethanesulfonic, hydroxymethane-and hydroxyethanesulfonic, and the like. (See for example, "Pharmaceutical Salts," *J. Pharm. Sci.*, 66 (1): 1-19 (1977)).

In a similar manner, the N-lower alkyl quaternary salts may be used in the pharmaceutical method of this invention as, for example, the N-methyl,1-azabicyclo[2.2.2]octane-3-carboxaldehyde oxime iodide.

The salts are prepared by contacting the free base form of the compounds of this invention with a sufficient amount of the desired acid or alkyl halide to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

The free base forms of the compounds of this invention differ somewhat from their respective salt forms in such physical properties as melting point and solubility in polar solvents, but the salts are otherwise equivalent to their respective free base forms for the purposes of the invention.

The compounds of the present invention are muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

The biological activity of compounds of the present invention was evaluated using a number of tests. The activity of compounds of this invention as central muscarinic binding site agonists and antagonists was measured. In the RQNB screening assay, which is described more fully by Mark Watson, et al, *J. Pharmocol. Exp. Ther.*, 237 (2): 411 (1986), rat cerebral cortex tissue was treated with radio-labeled quinuclidinyl benzilate, a known muscarinic binding site antagonist. The % inhibition concentration of test compound required to inhibit 50% of the binding of this muscarinic antagonist was then determined.

Similarly, in the RCMD screening assay, described more fully by T. W. Vickeroy, et al, *J. Pharmacol. Exp. Ther.*, 229 (3): 747 (1984), rat cerebral cortex tissue was treated with radio-labeled cis-methyldioxolane, a known muscarinic binding site agonist. The concentrations of test compounds required to inhibit 50% of the binding of this muscarinic agonist were then determined. These values are reported as % inhibition $IC_{50}$ concentration in Table 1 and demonstrate that the compounds of the present invention possess significant muscarinic activity.

In a second screening assay, designated SIS, the scopolamine induced swimming test, the ability of representative compounds of the present invention to reverse the hyperactive swimming behavior of laboratory rats given scopolamine was assessed. In this test, untreated rats will generally swim distances between 20 to 30 meters during a five minute test period. Rats given scopolamine at doses of 0.1 mg/kg develop a stereotypical swimming hyperactivity with the swimming distances generally increasing by 75-125% above baseline values. This swimming hyperactivity can be reversed by administration of physostigmine or the cholinergic agonist, arecoline. The effect of scopolamine is centrally mediated; the ability of a test compound to reverse the hyperactive swimming behavior induced by scopolamine is thus a measure of the central cholinergic activity of the compound.

The $ED_{50}$ for 1-azabicyclo[2.2.2]octane - 3-carboxaldehyde, O-methyloxime, required to demonstrate reversal of the scopolamine-induced hyper-active swimming activity in laboratory rats is 1.8 mg/kg(PO).

TABLE 1

| | | | | | | |
|---|---|---|---|---|---|---|
| | | | | | $IC_{50}$ | |
| $R_1$ | $R_2$ | | double bond | (Nanomolar) or % Inhib. | | |
| | $R_3$ is hydrogen | | | RQNB | | RCMD |
| Hydrogen | Methyl | | No | 1365 | | 11.8 |
| Hydrogen | 2-Propynyl | | No | 348 | | 27 |
| Hydrogen | Allyl | | No | 146 | | 117 |
| Methyl | Methyl | | No | 54% @ $10^{-6}$ M | | 90% @ $10^{-7}$ M |
| Methyl | 2-Propynyl | | No | 81% @ $10^{-6}$ M | | 78% @ $10^{-7}$ M |

In therapeutic use as agents for treating pain or for treating cerebral insufficiency, the compounds utilized in the pharmaceutical method of this invention are administered to the patient at dosage levels of from 0.007 to 7000 mg per day. For a normal human adult of approximately 70 kg of body weight, this translates into a dosage of from 0.0001 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of the present invention may also be co-administered when desired with anticholinergic agents, for example, atropine, methylatropine, glycopyrrolate, scopolamine, methylscopolamine, pirenzepine, or AF-DX-116, to reduce cholinergic side-effects.

The following preparative examples are provided to enable one skilled in the art to practice the invention. They are illustrative of the present invention and are not to be read as limiting the scope of the invention as it is defined by the appended claims.

EXAMPLE 1

Z- and E- 1-Azabicyclo[2.2.2]octane-3-carboxaldehyde, oxime

1-Azabicyclo[2.2.2]octane-3-carboxaldehyde was prepared by the method of Rubstov et al. (Khim. Geterosikl. Soedn. (1968), 4,881).

The aldehyde (3.39 g, 24.4 mmol) was dissolved in 50 ml of methanol. Hydroxylamine hydrochloride (1.9 g, 26.8 mmol) was added and the reaction was refluxed for 16 hours. The reaction was concentrated in vacuo to afford a white solid. The solid residue was dissolved in 15 ml of water which was made basic with solid potassium carbonate and extracted with chloroform (3×200 ml). The organic phase was dried over anhydrous magnesium sulfate and concentrated to afford 2.16 g of the title oxime (57%), mp 153°–158° C.

$C_8H_{14}N_2O$ Calcd: C 62.31; H, 9.15; N, 18.17. Found: C 62.05; H, 9.20; N 18.04.

Mass Spec: m/e 154.

$^1$H NMR: δ (CDCl$_3$) 1.38–1.96 (4H, m);2.45–3.3 (7H, m)6.78 (1H, d, Z,

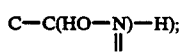

C—C(HO—N)—H);

7.44 (1H, d , E,

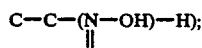

C—C—(N—OH)—H);

11.3 (1H, br.s)

$^{13}$C NMR: δ (CDCl$_3$) 21.37; 21.88; 23.78; 25.06; 26.54; 26.85, 32.44; 36.59; 46.57; 46.69; 47.11; 50.17; 52.16; 152.2, 153.95.

EXAMPLE 2

Z- and E-1-Azabicyclo[2.2.2]octane-3-carboxaldehyde, O-methyloxime, hydrochloride 1-Azabicyclo[2.2.2]octane-3-carboxaldehyde(1 g, 7.18 mmol) was dissolved in 10 ml of methanol. Methoxyamine hydrochloride (0.66 g, 7.9 mmol) was added and reaction was refluxed for 16 hours. The reaction was concentrated in vacuo to afford a white solid residue. The residue was dissolved in 15 ml of water which was made basic with solid potassium carbonate and extracted with ethyl acetate (3×100 ml). The organic phase was dried over magnesium sulfate to afford 1.05 g of a clear yellow oil which was converted to the title hydrochloride salt (1.05 g, 71%) by treatment with ethereal hydrogen chloride, mp 149°–152° C.

$C_9H_{17}ClN_2O$ Calc: C, 52.80; H, 8.37; N, 13.69. Found: C, 52.61; H, 8.40; N, 13.71.

Mass Spec: m/e 168.1 (M+ for free base).

$^1$H NMR: δ (CDCl$_3$) 1.73–3.70 (12H,m); 3.76 (3H, s, E, C—C(NOCH$_3$)—H); 3.80 (3H, s, Z,

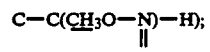

C—C(CH$_3$O—N)—H);

6.67–6.69 (1H, d, Z,

C—C(—N)—H);

7.28–7.29

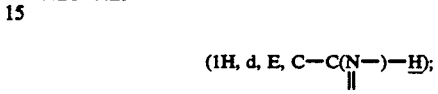

(1H, d, E, C—C(N—)—H);

12.07 (1H, br. s).

$^{13}$C NMR: δ (CDCl$_3$) 18.74, 23.6, 23.84, 34.57, 45.79, 46.02, 46.12, 47.25, 50.39, 62.01, 147.20, 149.19.

EXAMPLE 3

The procedure above was carried out for the synthesis of the following:

Z -and E- 1-Azabicyclo[2.2.2]octane-3-carboxaldehyde, O-ethyloxime, hydrochloride This was prepared by reacting 1-azabicyclo[2.2.2]octane-3-carboxaldehyde (1 g, 7.18 mmol) and ethoxyamine hydrochloride (0.77 g, 7.9 mmol) to afford the title product, 1.21 g (77%), mp 150°–152° C.

$C_{10}H_{19}ClN_2O$ Calc.: C, 54.91; H, 8.77; N, 12.81. Found: C, 54.41; H, 8.87; N, 12.63.

Mass Spec: m/e 182.1 (M+ for free base).

$^1$H NMR: δ CDCl$_3$) 1.23–1.28 (3H, triplet); 1.81–2.1 (4H, m); 2.24–2.28 (1H, m); 2.93–3.00 (1H, m); 3.23–3.45 (5H, m); 3.75–3.81 (1H, m); 4.07–4.14 (2H, quartet); 6.78–6.80 (1H, d, Z, C—C(—N)—H); 7.38–7.39 (1H, d, E, C—C(N—)—H); 12.18 (1H,br.s)

$^{13}$C NMR δ (CDCl$_3$) 14.38, 18.80, 23.64, 23.90, 34.73, 46.07, 69.85, 146.86.

EXAMPLE 4

E- and Z-1-Azabicyclo[2.2.2]octane-3-carboxaldehyde, O-2-propenyloxime, hydrochloride This was prepared by reacting 1-azabicyclo[2.2.2]octane-3-carboxaldehyde (2.36 g, 0.017 mol) and O-allylhydroxylamine hydrochloride hydrate (2.04 g, 0.0187 mol) to afford the title compound Yield 2.64 g (73%), mp 120°–122° C.

$C_{11}H_{19}ClN_2O$ Calc.: C, 57.26; H, 8.30; N, 12.14. Found: C, 57.00; H, 8.35; N, 12.15.

Mass Spec: m/e 194(M+ for free base).

$^1$H NMR: δ (CDCl$_3$) 1.82–2.09 (4H, m); 2.24–2.31 (1H, m); 2.92–3.04 (1H, m); 3.22–3.44 (5H, m); 3.70–3.80 (1H, m); 4.53–4.61 (2H, m); 5.21–5.35 (2H, m); 5.85–6.05 (1H, m); 6.83–6.85

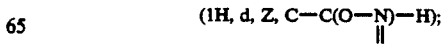

(1H, d, Z, C—C(O—N)—H);

7.45–7.47

(1H, d, E, C—C(N—O)—H)
         ‖

¹³C NMR: δ (CDCl₃) 18.358, 19.1, 22.92, 23.14, 34.22, 39.73, 40.02, 45.43, 45.63, 45.74, 46.82, 74.61, 74.97, 117.76, 133.22, 147.54, 149.42.

EXAMPLE 5

Z- and E- Azabicyclo[2.2.2]octane-3-carboxaldehyde, O-benzyloxime, hydrochloride This was prepared by reacting 1-azabicyclo[2.2.2]octane-3-carboxaldehyde (2 g, 14.4 mmol) and O-benzylhydroxylamine hydrochloride (2.52 g, 15.8 mmol) to afford the title product 2.68 g (66%), mp 156°-158° C.

$C_{15}H_{21}ClN_2O$ Calc C, 64.16; H, 7.54; N: 9.98. Found: C, 64.35; H, 7.58; N: 9.98.

Mass Spec: m/e 244.2 (M⁺ for free base).

¹H HNMR: δ (CDCl₃) 1.74–2.08 (4H, m); 2.21–2.26 (1H, m); 2.94–3.01 (1H, m); 3.15–3.42 (5H, m); 3.64–3.74 (1H, m); 5.07

(2H, s, E, C—C(N—OCH₂—)—H);
         ‖

5.11

(2H, s, Z, C—C(—CH₂O—N)—H);
         ‖

6.87–6.90

(1H, d, Z, C—C(O—N)—H);
         ‖

7.34 (5H, s, Ar); 7.46–7.49

(1H, d, E, C—C(N—O)—H)
         ‖

¹³C NMR: δ (CDCl₃/DMSO) 18.04, 18.84, 22.41, 22.65, 22.88, 23.11, 30.72, 33.99, 45.16, 45.36, 45.50, 46.52, 49.58, 75.56, 75.83, 127.43, 127.51, 127.56, 127.81, 127.89, 136.55, 147.85, 149.59.

EXAMPLE 6

E- and Z-1-Azabicyclo[2.2.2]octane-3-carboxaldehyde, O-propyloxime, hydrochloride This was prepared by reacting 1-azabicyclo[2.2.2]octane-3-carboxaldehyde (1.5 g, 10.8 mmol) and O-propylhydroxylamine hydrochloride (1.25 g, 11.2 mmol) to afford the title product, 1.87 g (84%), mp 157°-159° C.

$C_{11}H_{21}ClN_2O$ Calc.: C, 56.76; H, 9.09; N, 12.04. Found: C, 56.46; H, 9.26; N, 11.91.

Mass Spec: m/e 196.2 (M⁺ for free base).

¹H NMR: δ (CDCl₃) 0.89–0.97 (3H, triplet); 1.56–1.74 (2H, sextet); 1.83–2.14 (4h, m); 2.24–2.36 (1H, m); 2.96–3.04 (1H, m); 3.17–3.63 (5H, m); 3.70–3.80 (1H, m); 3.96–4.04 (2H, triplet); 6.80–6.82

(1H, d, Z, C—C(O—N)—H);
         ‖

7.40–7.42

(1H, d, E, C—C(N—O)—H)
         ‖

¹³C NMR: δ (CDCl₃) 9.97, 18.60, 22.02, 23.41, 23.69, 34.47, 45.89, 45.99, 47.09, 75.64, 146.80.

EXAMPLE 7

E- and Z- 1-Azabicyclo[2.2.2]octane-3-carboxaldehyde, O-(1-methylethyl) oxime, hydrochloride This was prepared by reacting 1-azabicycle[2.2.2]octane-3-carboxaldehyde (1.9 g, 13.7 mmol) and O-isopropyl hydroxylamine hydrochloride (1.56 g, 14.0 mmol) to afford the title product, 2.37 g (88%), mp 146°-150° C.

$C_{11}H_{21}ClN_2O \cdot \frac{1}{4} H_2O$ Calc.: C, 55.68, H, 9.13; N, 11.81. Found: C, 55.50, H, 8.92; N, 12.19.

¹H NMR: δ (CDCl₃) 1.2–1.24 (6H, d); 1.82–2.13 (4H, m); 2.22–2.28 (1H, m); 2.94–3.03 (1H, m); 3.25–3.51 (5H, m); 3.72–3.82 (1H, m); 4.26–4.39 (1H, septet); 6.77–6.79

(1H, d, Z, C—C(O—N)—H);
         ‖

7.36–7.38

(1H, d, E, C—C(N—O)—H)
         ‖

¹³C NMR: δ (CDCl₃) 19.31, 21.89, 24;11, 24.4, 35.27, 46.61, 47.84, 76.29, 147.04.

EXAMPLE 8

E- and Z-1-Azabicyclo[2.2.2]octane-3-carboxaldehyde, O-propynyloxime, hydrochloride This was prepared by reacting 1-azabicyclo[2.2.2]octane-3-carboxaldehyde (1.61 g, 11.6 mmol) and O-propargylhydroxylamine hydrochloride (1.25 g, 11.6 mmol) to afford the title product, 1.6 g (60%), mp 138°-141° C.

$C_{11}H_{17}ClN_2O$ Calc.: C, 57.76; H, 7.49; N, 12.25. Found: C, 57.58; H, 7 64; N, 12.28.

Mass Spec: m/e 192 (M⁺ for free base).

¹H NMR: δ (CDCl₃) 1.77–2.08 (4H, m); 2.20–2.41 (1H, m); 2.42–2.48 (1H, m); 2.93–3.02 (1H, m); 3.11–3.59 (5H, m); 3.66–3.75 (1H, m); 4.59–4.61

(2H, d, E, C—C(N—OCH₂—)—H);
         ‖

4.62–4.63

(2H, d, Z, C—C(—CH₂O—N)—H);
         ‖

6.89–6.92

(1H, d, Z, C—C(O—N)—H);
            ||

7.43–7.45

(1H, d, E, C—C(N—O)—H);
            ||

11.98 (1H, br. s).

$^{13}$C NMR: δ (CDCl$_3$) 18.69, 19.43, 23.09, 23.24, 23.49, 23.66, 31.31, 34.61, 45.76, 45.95, 46.05, 47.07, 50.06, 61.62, 61.82, 74.80, 74.95, 76.35, 78.99, 149.20, 151.08.

EXAMPLE 9

3-Cyano-1-azabicyclo[2.2.2]octane

3-Quinuclidinone (28.8 g, 0.23 mmol) and tosylmethyl isocyanide (58.4 g, 0.30 mol) were dissolved in 23 ml of absolute ethanol and 800 ml of dimethoxyethane and cooled to 0° C. Potassium t-butoxide (64.4 g, 0.57 mol) was added portionwise, and the reaction continued stirring at 0° C. for 30 minutes, then heated at 40° C. for 30 minutes. The reaction was cooled to room temperature and stirred for 16 hours. The reaction was filtered and the filtrate was concentrated in vacuo to afford a clear, golden brown oil (50 g) which was chromatographed on alumina eluting with ethyl acetate thus affording the title product, 23.3 g (74%).

EXAMPLE 10

1-Azabicyclo]2.2.2]octane-3-ethanone

An ethereal solution (3.0M) of methyl magnesium bromide (49 ml, 0.147 mol) was added to 80 ml of dry benzene and the ether was distilled off giving a turbid solution. 3-Cyano-1-azabicyclo[2.2.2]octane(10 g, 0.073 mol) in 25 ml of benzene was added to the turbid solution and refluxed for 3 hours. The reaction was quenched with 20 ml of 6N hydrochloric acid at reflux for 6 hours. An orange solid resulted which was separated by filtration and dissolved in 100 ml of water. The aqueous solution was basified with solid potassium carbonate and extracted with chloroform (3×250 ml). The organic phase was dried over solid potassium carbonate and concentrated in vacuo to afford a red-orange oil which was dissolved into ether, filtered, and concentrated to afford the title ketone product (8.3 g, 73%).

$^1$H NMR: δ (CDCl$_3$) 1.3–1.75 (5H, m); 2.13 (3H, s); 2.55–2.90 (6H, m); 3.15–3.42 (1H, m).

EXAMPLE 11

Ethanone,(1-azabicyclo[2.2.2]octane-3-yl), O-ethyl oxime, hydrochloride

This was prepared by reacting 1-azabicyclo[2.2.2]octane-3-ethanone (1.0 g, 6.53 mmol) and ethoxyamine hydrochloride (0.64 g, 6.53 mmol) to afford the product, 0.97 g (63.8%).

$C_{11}H_{21}ClN_2O \cdot \frac{1}{4} H_2O$ Calc.: C, 55.68; H, 9.13; N, 11.81. Found: C, 55.90; H, 8.80; N, 11.66.

Mass Spec: m/e 196.14(M+ for free base).

$^1$H NMR: δ (CDCl$_3$/DMSO) 1.21–1.26 (3H, t); 1.86–2.32 (4H, m); 2.86) 1H, m); 3.20–3.43 (6H, m); 3.91–3.97 (1H, m); 4.05–4.13 (2H, q); 11.61 (1H, br. s).

$^{13}$C NMR: δ (CDCl$_3$/DMSO) 14.13, 14.40, 18.26, 22.72, 23.27, 45.48, 46.37, 68.74, 152.57.

EXAMPLE 12

Ethanone,(1-azabicyclo[2.2.2]octane-3-yl), O-propyloxime, hydrochloride

This was prepared by reacting 1-azabicyclo[2.2.2]octane-3-ethanone (1 g, 6.53 mmol) and O-propyl hydroxylamine hydrochloride (0.73 g, 6.53 mmol) to afford the product 0.78 g (48.4%).

$C_{12}H_{23}ClN_2O$ Calc.: C, 58.40; H, 9.39; N, 11.35. Found: C, 57.99; H, 9.40; N, 11.27.

Mass Spec: m/e 210.2 (M+ for free base).

$^1$H NMR: δ (CDCl$_3$) 0.89–0.96 (3H, t); 1.57–1.78 (2H, sextet); 1.86 (3H, s); 2.05–2.13 (2H, m); 2.29–2.32 (2H, m); 2.81–2.84 (1H, m); 3.21–3.41 (6H, m); 3.97–4.05 (3H, t and m), 11.8(1H, br.s).

$^1$H NMR: δ (CDCl$_3$) 10.24, 14.40, 18.68, 22.40, 23.20, 23.78, 40.23, 45.83, 46.08, 46.79, 75.65, 152.76.

EXAMPLE 13

Ethanone, (1-azabicyclo[2.2.2]octane-3-yl), O-2-propenyloxime, hydrochloride

This was prepared by reacting 1-azabicyclo[2.2.2]octane-3-ethanone (1 g, 6.35 mmol) and O-allylhydroxylamine hydrochloride hydrate to afford the product, 0.97 g (61%).

$C_{12}H_{21}ClN_2O$ Calc.: C, 57.75; H, 8.60; N, 11.27. Found: C, 57.82 ; H, 8.69; N, 11.24.

Mass Spec: m/e 208.2(M+ for free base).

$^1$H NMR: δ CDCl$_3$) 1.77–1.98 (2H, m); 1.89 (3H, s); 2.02–2.12 (2H, m); 2.86 (1H, m); 3.24–3.38 (6H, m); 3.95–4.03 (1H, m); 4.55–4.57 (2H, d); 5.21–5.31 (2H, m); 5.87–6.02 (1H, m); 11.9 (1H, br. s).

$^{13}$C NMR: δ (CDCl$_3$) 14.57, 18.67, 23.2, 23.78, 40.27, 45.80, 46.1, 46.80, 74.89, 117.51, 134.14, 153.62.

EXAMPLE 14

3-Hydroxymethyl-1-azabicyclo[2.2.2]oct-2-ene

3-Carbomethoxy-1-azabicyclo[2.2.2]oct-2-ene was prepared by the method reported by Grob (Helv. Chim. Acta (1954), 37, 1689).

The ester (14 g, 68.7 mmol) was dissolved in 100 ml of dry toluene. A 1.5M solution of DIBAL in toluene (95 ml, 143 mmol) was added dropwise to this solution at room temperature. The reaction was stirred for 1.5 hours. This was quenched by adding 10 ml of methanol, followed by 20 ml of methanol-water (1:1), and finally 10 ml of water. The white precipitate was separated by filtration and the filtrate concentrated in vacuo to afford a viscous liquid. This was dissolved in warm ether, filtered, and concentrated to afford the product as a white crystalline solid, 7.4 g (79%), mp 79°–82° C. (Lit. 80°–82° C. in U.S. Pat. No. 4,467,095).

$C_8H_{13}NO$ Calc.: C, 69.03; H, 9.41; N, 10.06. Found: C, 68.71; H, 9.55; N, 10.06.

Mass Spec: m/e 139.0.

$^1$H NMR: δ (CDCl$_3$) 1.45 (2H, m); 1.66 (2H, m); 2.55 (2H, m); 2.62 (1H, m); 2.9 (2H, m); 4.18 (2H, d); 4.70 (1H, br.s); 6.35 (1H, d).

$^{13}$C NMR: 27, 27.5, 48, 62, 135, 148.

IR(cm): 1652 (C=C stretch).

EXAMPLE 15

1-Azabicyclo[2.2.2]oct-2-ene-3-carboxaldehyde

Freshly distilled oxalyl chloride (4.2 ml, 47.3 mmol) was dissolved in 80 ml of methylene chloride and cooled to −78° C. A solution of DMSO (6.7 ml, 94.6 mmol) in 20 ml of methylene chloride was added dropwise to the cooled solution. After stirring 10 minutes, a solution of 3-hydroxymethyl-1-azabicyclo[2.2.2]oct-2-ene (6 g, 43 mmol) in 20 ml of methylene was added dropwise and the reaction stirred for 1 hour. Triethylamine (30 ml, 215 mmol) was added to the reaction and the reaction was slowly warmed to room temperature, then poured into 200 ml of water and the organic phase separated. The aqueous phase was extracted with methylene chloride (3×250 ml) and the combined organic phases were washed with 10% sodium carbonate (2×150 ml), dried over anhydrous sodium sulfate, and concentrated in vacuo to afford a yellow liquid. The crude liquid was stirred in diethyl ether, filtered, and concentrated to afford a clear, yellow liquid (4 g) which was distilled (42° C., 0.25 mm Hg) to give the product as a clear, colorless liquid (2.4 g, 40%).

$C_8H_{11}NO$ Calc.: C, 70.04; H, 8.08; N, 10.21. Found: C, 69.05 H, 8.27; N, 9.90.

Mass Spec: m/e 137.1.

$^1$H NMR: δ (CDCl$_3$) 1.35 (2H, m); 1.75 (2H, m); 2.55 (2H, m); 3.1 (2H, m); 3.25 (1H, m); 7.42 (1H, s); 9.6 (1H, s).

$^{13}$C NMR: δ (CDCl$_3$) 23 (bridgehead C); 27 (2C, aliphatic at pos. 3 & 5); 49 (2C, aliphatic C bonded to hetero atom, N); 150 (vinyl C bonded to carbonyl); 162 (vinyl C bonded to hetero atom, N); 188 (carbonyl carbon).

IR(cm$^{-1}$): 1680(C=O stretch); 1607 (C=C stretch).

EXAMPLE 16

1-Azabicyclo[2.2.2]oct-2-ene-3-carboxaldehyde oxime, hydrochloride

1-Azabicyclo[2.2.2]oct-2-ene-3-carboxaldehyde (1 g, 7.29 mmol) was dissolved in 50 ml of methanol. Hydroxylamine hydrochloride was added to the solution and the reaction was stirred at room temperature for 18 hours. The reaction was concentrated in vacuo to afford a white crystalline residue. The crystalline residue was suspended in 50 ml of isopropanol and refluxed for 15 minutes A crystalline material separated to afford the desired oxime (1.08 g, 75%), mp 227°–229° C.

$C_8H_{13}ClN_2O$ Calc.: C, 50.93; H, 6.95; N, 14.85. Found: C, 50.98; H, 6.95; N, 14.82.

Mass Spec: m/e 152.1 (M+ for free base).

$^1$H NMR: δ (DMSO) 1.68 (2H, m); 2.04 (2H, m); 3.06 (2H, m); 3.62 (2H, m); 6.93 (1H, s); 7.85 (1H, s); 11.70 (1H, s); 12.45 (1H, s).

$^{13}$C NMR: δ (DMSO) 22.59; 24.26; 49.45; 129.3; 141.89; 143.15.

EXAMPLE 17

1-Azabicyclo[2.2.2]oct-2-ene-3-carboxaldehyde, O-methyl oxime, hydrochloride

1-Azabicyclo[2.2.2]oct-2-ene-3-carboxaldehyde (2.34 g, 17.1 mmol) was dissolved in 100 ml of methanol. Methoxyamine hydrochloride (1.42 g, 17.1 mmol) was added and the reaction was stirred at room temperature for 16 hours. The reaction was concentrated in vacuo to afford a white solid which was dissolved in 75 ml of water, basified with solid potassium carbonate, and extracted with ethyl acetate (3×100 ml). The organic phase was dried over anhydrous sodium sulfate and concentrated in vacuo to afford 2.17 g of a clear liquid which was chromatographed on silica gel eluting with acetone (R$_f$=0.2) thus affording 1.19 g of a clear, colorless liquid which was converted to the title hydrochloride salt (1.17 g, 33%) by treatment with ethereal hydrogen chloride, mp 202°–204° C.

$C_9H_{15}ClN_2O$ Calc.: C, 53.33; H, 7.46; N, 13.82. Found: C, 53.13; H, 7.48; N, 13.72.

Mass Spec: m/e 166 (M+ for free base).

$^1$H) NMR: δ (CDCl$_3$) 1.78 (2H, m); 2.10 (2H, m); 3.15 (2H, m); 3.72(3H, m); 3.97 (3H, s); 6.97 (1H, d); 7.77 (1H, s); 13.66 (1H, br. s).

$^{13}$C NMR: δ (CDCl$_3$) 22, 24, 50, 63, 129, 142, 143.

EXAMPLE 18

1-Azabicyclo[2.2.2]oct-2-ene-3-carboxaldehyde, O-propynyl oxime, hydrochloride

1-Azabicyclo[2.2.2]oct-2-ene-3-carboxaldehyde (1 g, 7.29 mmol) was dissolved in 50 ml of methanol. O-propargyl hydroxylamine hydrochloride was added to the reaction, and the reaction was stirred at room temperature for 16 hours. The reaction was concentrated in vacuo to afford a gummy solid which was recrystallized from isopropanol-isopropyl ether to give the O-propargyl oxime hydrochloride (0.91 g, 55%), mp 175°–176° C., dec.

$C_{11}H_{15}ClN_2O$ Calc.: C, 58.28; H, 6.67; N, 12.36. Found: C, 58.13; H, 6.65; N, 12.37.

Mass Spec: m/e 190.1 (M+ for free base).

$^1$H NMR: δ (CDCl$_3$) 1.77 (2H, m); 2.02 (2H, m); 2.50 (1H, m); 3.13 (2H, m); 3.59 (2H, m); 3.72 (1H, m); 4.72 (2H, d); 6.96 (1H, d); 7.79 (1H, s); 14.0 (1H, br. s).

$^{13}$C NMR: δ (CDCl$_3$) 23.09, 24.69, 50.11, 62.39, 75.29, 77.91, 130.37, 141.69, 143.25.

EXAMPLE 19

The above procedure was used for the synthesis of the following:

1-Azabicyclo[2.2.2]oct-2-ene-3-carboxaldehyde, O-2-propenyl oxime, hydrochloride This was prepared by reacting 1-azabicyclo[2.2.2]oct-2-ene-3-carboxaldehyde and O-allylhydroxylamine hydrochloride hydrate to afford the title product, 0.95 g (56.9%). mp 178°–182° C., dec.

$C_{11}H_{17}ClN_2O$ Calc.: C, 55.57; H, 7.63; N, 11.78. Found: C, 55.83; H, 7.70; N, 11.81.

Mass Spec: m/e 192.1 (M+ for free base).

$^1$H NMR: δ (CDCl$_3$) 1.77 (2H, m), 2.08 (2H, m); 3.16 (2H, m); 3.65 (2H, m); 3.72 (1H, m); 4.67 (2H, d); 5.29 (2H, m); 5.97 (1H, m); 6.97 (1H, s); 7.81 (1H, s).

$^{13}$C NMR: δ (CDCl$_3$) 23.2, 24.8, 50.3, 25.96, 118.65, 129.55, 133.05, 142.13, 142.19.

EXAMPLE 20

1-Azabicyclo[2.2.2]oct-2-ene-3-carboxadehyde, O-ethyl oxime, hydrochloride

This was prepared by reacting 1-azabicyclo[2.2.2]oct-2-ene-3-carboxaldehyde (1 g, 7.29 mmol) and ethoxyamine hydrochloride to afford the title product, 0.60 g (38%) after recrystallization from isopropanol-isopropyl ether; mp 197°–198° C., dec.

$C_{10}H_{17}ClN_2O \cdot \frac{1}{4} H_2O$ Calc.: C, 54.29; H, 7.97; N, 12.66. Found: C, 53.96; H, 7.76; N, 12.48.

MS: m/e 180.1 (M+ for free base).

$^1$H NMR: δ (CDCl$_3$) 1.29 (3H, triplet); 1.78 (2H, m); 2.10 (2H, m); 3.16 (2H, m); 3.68 (3H, 2 multiplets); 4.20 (2H, quartet); 6.94 (1H, d); 7.76 (1H, s); 13.6 (1H, s).

$^{13}$C NMR: δ (CDCl$_3$) 14.4, 23.2, 24.8, 50.3, 70.7, 129.1, 141.6, 142.3.

EXAMPLE 21

1-Azabicyclo[2.2.2]oct-2-ene-3-carboxyaldehyde, O-propyl oxime, hydrochloride

This was prepared by reacting 1-azabicyclo[2.2.2]oct-2-ene-3-carboxaldehyde (1 g, 7.29 mmol) and O-propylhydroxylamine hydrochloride (0.85 g, 7.29 mmol) to afford, after recrystallization from isopropanol-isopropyl ether, 0.65 g (38%) of the title product; mp 197°–199° C., dec.

$C_{11}H_{19}ClN_2O$ Calc.: C, 56.16; H, 8.36; N, 11.91. Found: C, 56.12; H, 8.20; N, 11.88.

MS: m/e 194.2 (M+ for free base).

$^1$H NMR: δ (CDCl$_3$) 0.96 (3H, t); 1.70 (2H, sextet); 1.79 (2H, m); 2.10 (2H, m); 3.16 (2H, m); 3.7 (3H, 2m); 4.11 (2H, t); 6.94 (1H, d); 7.78 (1H, s); 13.6 (1H, br. s).

$^{13}$C NMR: δ (CDCl$_3$) 10.21, 22.14, 23.16, 24.74, 50.29, 76.74, 129.07, 141.54, 142.31.

EXAMPLE 22

1-Azabicyclo[2.2.2]oct-2-ene-3-carboxyaldehyde, O-(1-methylethyl) oxime, hydrochloride This was prepared by reacting 1-azabicyclo[2.2.2]oct-2-ene-3-carboxaldehyde (1 g, 7.29 mmol) and O-isopropylhydroxylamine hydrochloride (0.85g, 7.65 mmol) to afford 0.73 g (43%) of the title product after recrystallization from isopropanol-isopropyl ether, mp 206°–208° C., dec.

$C_{11}H_{19}ClN_2O·\frac{1}{4}H_2O$ Calc.: C, 56.16; H, 8.36; N, 11.91. Found: C, 56.12; H, 8.14; N, 11.89

MS: m/e 194.1 (M+ for free base).

$^1$H NMR: δ (CDCl$_3$) 1.27 (6H, d); 1.78 (2H, m); 2.09 (2H, m); 3.16 (2H, m); 3.67 (2H, m); 3.75 (1H, m); 4.42 (1H, septet); 6.92 (1H, d); 7.74 (1H, s); 13.65 (1H, br. s).

$^{13}$C NMR: δ (CDCl$_3$) 21.38, 23.19, 24.76, 50.32, 77.02, 128.81, 141.21, 142.52.

EXAMPLE 23

1-Azabicyclo[2.2.2]oct-2-ene-3-carboxaldehyde, O-benzyloxime, hydrochloride

This was prepared by reacting 1-azabicyclo[2.2.2]oct-2-ene-3-carboxaldehyde (1 g, 7.29 mmol) and O-benzylhydroxylamine hydrochloride (1.16 g, 7.29 mmol) to afford 0.83 g (41%) of the title product, after recrystallization from isopropanol-isopropyl ether; mp 203°–204° C., dec.

$C_{15}H_{19}ClN_2O·\frac{1}{4}H_2O$ Calc.: C, 63.60; H, 6.94; N, 9.89. Found: C, 63.29; H, 6.76; N, 9.79.

MS: m/e 242.1 (M+ for free base).

$^1$H NMR: δ (CDCl$_3$) 1.76 (2H, m); 2.06 (2H, m); 3.14 (2H, m); 3.65 (2H, m); 3.71 (1H, m); 5.18 (2H, s); 6.95 (1H, d); 7.36 (5H, s); 7.82 (1H, s); 13.7 (1H, br. s).

EXAMPLE 24

3-(1-Hydroxyethyl)-azabicyclo[2.2.2]oct-2-ene 1-azabicyclo[2.2.2]-2-ene-3-carboxaldehyde (2 g, 14.6 mmol) was dissolved in 50 ml of dry tetrahydrofuran and cooled to −15° C. A solution of 1.4M methyl lithium in diethyl ether (11.5 ml, 16.04 mmol) was added dropwise. The reaction was warmed to room temperature and 5 ml of saturated ammonium chloride was added to the reaction. The reaction was filtered and concentrated in vacuo to afford a dark brown oil which was chromatographed on alumina eluting with CHCl$_3$:MeOH (9:1) to give 1.00 g (45%) of the title alcohol product.

$^1$H NMR: δ (CDCl$_3$) 1.28 (3H, d); 1.35–1.85 (4H, m); 2.4–2.95 (5H, m); 4.15–4.55 (1H, q); 4.4 (1H, s); 6.3 (1H, s).

EXAMPLE 25

Ethanone, 1-(1-Azabicyclo[2.2.2]oct-2-ene-3-yl)-,

Oxalyl chloride (0.60g, 7.23 mmol) was dissolved in 20 ml of methylene chloride and cooled to −78° C. Dimethyl sulfoxide (1 ml, 14.5 mmol) was added dropwise and the reaction was stirred for 10 minutes. A solution of 3 -(1-hydroxyethyl)-1-azabicyclo[2.2.2]oct-2-ene (1 g, 6.6 mmol) in 20 ml of methylene chloride was added dropwise. After 1 hour of stirring at −78° C., triethylamine (4.6 ml, 32.9 mmol) was added to the reaction and the reaction was warmed to room temperature. The reaction was poured into 50 ml of water and the organic phase was separated. The aqueous phase was extracted with methylene chloride (2×100 ml). The organic phases were combined, washed with 10% Na$_2$CO$_3$, dried over anhydrous potassium carbonate, and concentrated to afford a yellow oil which was chromatographed on silica gel eluting with CHCl$_3$:MeOH (9:1) to give the title product, 0.52 g (52%).

$^1$H NMR: δ (CDCl$_3$) 1.2–1.8 (4H, m); 2.25 (3H, s); 2.3–3.3 (5H, m); 7.35 (1H, d).

EXAMPLE 26

Ethanone, (1-azabicyclo[2.2.2]oct-2-ene-3-yl), O-methyl oxime, hydrochloride

Ethanone,1-(1-azabicyclo[2.2.2]oct-2-ene-3-yl- (0.52 g, 3.44 mmol) and methoxyamine hydrochloride (0.29 g, 3.44 mmol) were dissolved in 50 ml of methanol and stirred at room temperature for 16 hours. The reaction was concentrated in vacuo to afford a white solid residue which was recrystallized by isopropanol-isopropyl ether to give the title hydrochloride (0.56 g, 75%), mp 217°–222° C., dec.

$C_{10}H_{17}ClN_2O·\frac{1}{4} H_2O$ Calc.: C, 54.29; H, 7.97; N, 12.66. Found: C, 54.55; H, 7.88; N, 12.98.

Mass Spec: m/e 180.1 (M+ for free base).

$^1$H NMR: δ (CDCl$_3$ 1.67–1.79 (2H, m); 1.95 (3H, s); 2.00–2.10 (2H, m); 3.05–3.15 (2H, m); 3.52–3.63 (2H, m); 3.89 (1H, s); 3.98 (3H, s); 6.92 (1H, d); 13.46 (1H, br. s).

We claim:

1. An azabicycle ring compound of Formula Ia

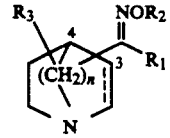

wherein the —C(=NOR$_2$)R$_1$ is attached at either carbon atom three or four of the azabicyclo ring, and the attachment of the OR$_2$ group to the nitrogen atom is configured either Z- or E- to the azabicyclo ring;

n is 1 to 4;

R$_1$ is hydrogen; alkyl of from 1 to 6 carbon atoms optionally substituted with hydroxy or alkoxyl of from 1 to 4 carbon atoms; alkenyl of from 1 to 6 carbon atoms optionally substituted with hydroxy or alkoxyl of from 1 to 4 carbon atoms; alkynyl of from 1 to 6 carbon atoms optionally substituted with hydroxy or alkoxyl of from 1 to 4 carbon atoms; cycloalkyl of from 3 to 8 carbon atoms; —A—C(=O)—O—R$_4$ where A is a bond or is a hydrocarbon chain of from 1 to 4 carbon atoms and when containing two or more carbon atoms may contain one double bond and where $R_4$ is alkyl of from 1 to 6 carbon atoms;

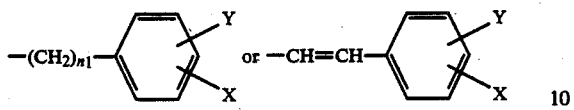

where $n_1$ is zero to four and X and Y are independently selected from hydrogen, fluorine, chlorine, bromine, hydroxy, straight or branched alkyl of from 1 to 3 carbon atoms, or alkoxyl of from 1 to 4 carbon atoms;
$R_2$ is selected from

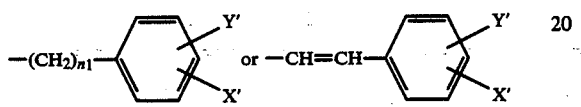

where $n_1$ is zero to four and X' and Y' are independently selected from hydrogen, fluorine, chlorine, bromine, hydroxy, alkyl of from 1 to 3 carbon atoms, and alkoxyl of from 1 to 4 carbon atoms; or —C(=O)—NR$_5$R$_6$ where $R_5$ and $R_6$ are independently selected from hydrogen, alkyl of from 1 to 4 carbon atoms or phenyl; and $R_3$ is selected from hydrogen; alkyl of from 1 to 6 carbon atoms; hydroxy; alkoxyl of from 1 to 4 carbon atoms; alkylcarbonyl of from 2 to 12 carbon atoms; NH$_2$; NH(C$_{1-4}$alkyl); N(C$_{1-4}$alkyl)$_2$; NHCO(C$_{1-4}$alkyl); and NHCOOCH$_3$;

or a pharmaceutically acceptable acid addition salt of said compound.

2. An E- or Z-azabicyclo-octane- or azabicyclo-octene-oxime compound according to claim 1 having the formula

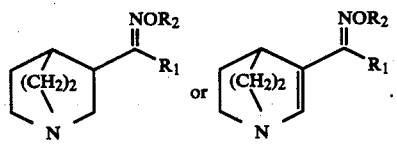

3. An E- or Z-azabicyclo-octane- or azabicyclo-octene-oxime compound according to claim 1 having the formula

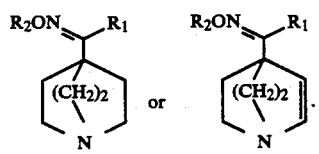

4. An E- or Z-azabicyclo-heptane- or azabicyclo-heptene-oxime compound according to claim 1 having the formula

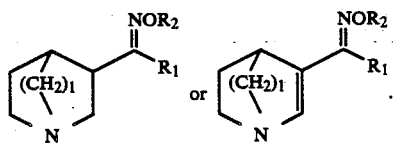

5. An E- or Z-azabicyclo-heptane- or azabicyclo-heptene-oxime compound according to claim 1 having the formula

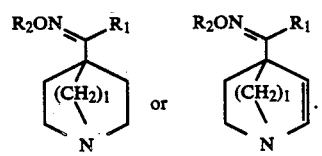

6. A compound having Formula Ia according to claim 1 where $R_1$ is selected from straight or branched alkyl of from 1 to 6 carbon atoms optionally substituted with hydroxy or alkoxyl of from 1 to 4 carbon atoms;
straight or branched alkenyl of from 1 to 6 carbon atoms optionally substituted with hydroxy or alkoxyl of from 1 to 4 carbon atoms;
straight or branched alkynyl of from 1 to 6 carbon atoms optionally substituted with hydroxy or alkoxyl of from 1 to 4 carbon atoms; or
cycloalkyl of from 3 to 8 carbon atoms.

7. A compound having Formula Ia according to claim 1 where $R_1$ is —A—C(=O)—OR$_4$ where A is a bond or is a hydrocarbon chain of from 1 to 4 carbon atoms and when containing two or more carbon atoms may contain one double bond and $R_4$ is alkyl of from 1 to 6 carbon atoms.

8. A compound having Formula Ia according to claim 1 where $R_2$ is —C(=O)—NR$_5$R$_6$ where $R_5$ and $R_6$ are independently selected from hydrogen and alkyl of from 1 to 4 carbons or phenyl.

9. A pharmaceutical composition useful for alleviating pain in a mammal or for the treatment of the symptoms of cognitive decline in an elderly patient comprising an effective amount of a compound as defined in claim 1 together with a pharmaceutically acceptable carrier.

10. A method of alleviating pain in a mammal comprising administering to a mammal in need of such treatment an analgesically effective amount of a compound in accordance with claim 1 together with a pharmaceutically acceptable carrier.

11. A method of treating the symptoms of cognitive decline in an elderly patient comprising administering to a patient in need of such treatment a cholinergically effective amount of a compound as defined in claim 1 in combination with a pharmaceutically acceptable carrier.

* * * * *